United States Patent [19]

Rademacher

[11] Patent Number: 4,901,576
[45] Date of Patent: Feb. 20, 1990

[54] ACOUSTIC LEAK-DETECTION SYSTEM
[75] Inventor: Paul E. Rademacher, Setauket, N.Y.
[73] Assignee: Robotic Vision Systems, Inc., Hauppauge, N.Y.
[21] Appl. No.: 179,579
[22] Filed: Apr. 8, 1988
[51] Int. Cl.[4] ............................................. G01N 29/00
[52] U.S. Cl. ........................................ 73/592; 73/588
[58] Field of Search ................. 73/588, 592, 602, 600, 73/618, 619, 40.5 A, 40; 364/507

[56] References Cited

U.S. PATENT DOCUMENTS

| | | | |
|---|---|---|---|
| 4,384,489 | 5/1983 | Crutzen et al. | 73/602 |
| 4,603,584 | 8/1986 | Bartle et al. | 73/602 |
| 4,719,801 | 1/1988 | Blaser et al. | 73/592 |

Primary Examiner—John Chapman
Attorney, Agent, or Firm—Max Fogiel

[57] ABSTRACT

Leak detector arrangement for the detection of small openings in car bodies or other enclosures or containers which may permit undesired passage of water, fumes, or other fluids in which phase coded or linearly frequency modulated sound waves are directed towards potential leak areas. The portion of these waves which pass through the leak openings is received, and these signals are processed so as to discriminate these leak signals from other sound waves normally entering the receiver from other parts or from other sources. The discriminated signals are compared with a threshold so as to determine the absence or presence of a leak.

15 Claims, 6 Drawing Sheets

4,901,576

ACOUSTIC LEAK-DETECTION SYSTEM

BACKGROUND OF THE INVENTION

It is a part of the production process of building automobiles to examine the bodies for breaks in seals where parts are joined together that allow gases (e.g. exhaust fumes) or liquids (e.g. rain water) to leak into the interior compartments. Testing for the presence of such leaks has been accomplished by spraying water on the bodies and observing where water seeps through. An alternative method has employed emitting sound on one side of the compartment wall and listening with a microphone on the other side for where the sound may leak through.

In using sound to detect leaks, the system has to contend with ambient noises of the factory, alternate sound paths (such as through the windows), transmission of sound through the compartment wall, and indirect leakage paths (where the sound leaks into a channel, travels within the channel and exits into the compartment). These many paths that the sound travels is referred to as the multipath problem. By sinusoidally frequency modulating (FM) the sound, attempts were made to prevent the interfering multipath energy from nulling out the signal, but this was only effective on closed cavity applications. In open cavities such as an automobile chassis, energy escapes through the window areas, reflects off surrounding structures and interferes with the primary path energy with small attenuation.

Typical frequencies employed in the prior art were in the 35-40 KHZ range which enabled substantial transmission of energy through the compartment walls. Also, at these operating frequencies, the factory noise inband interference had been substantial. Setting the systems up consisted of manually adjusting detection thresholds to bring false alarms to acceptable levels. No range discrimination was employed.

SUMMARY OF THE INVENTION

It is an object of the present invention to overcome the prior art disadvantges. In particular, it is the object of the present invention to provide a method and an arrangement for detecting small holes and spaces between adjoining surfaces through which gases or liquids may flow (leak). It is a further object to provide a method for automatic leak decision thresholding and automatic verification of component performance.

In keeping with these objects and with still others which will become apparent as the description proceeds, the important characteristics of the invention are: ability to detect relatively small leaks in a factory environment, automatic learning, automatic verification of operability, and tolerance for small robot path errors.

The present invention is comprised as follows: acoustic transducers are deployed strategically within a compartment or around the exterior of a compartment. Microphone pickups are mounted on robot arms and the robots are taught paths that scan the microphones along seams of the compartment. The transducers generate higher frequency sound than the prior art systems and phase encoding is added. By increasing the operating frequency, the inband factory noise interference experiences greater atmospheric attenuation, and less sound is transmitted directly through the compartment walls. Phase encoding enables the received signal to be cross-correlated with the transmitted signal to provide range and multipath discrimination. The signal signature of a leak-free compartment is recorded to automatically learn a system reference. Then the inspection of compartments relies on the comparison of the received signal with the reference. The reference is shifted a small amount to maximize correlation with the received signal to accommodate small spatial changes in the compartment location/orientation and changes in the velocity of propagation of sound. Leaks are indicated by significant signal increases in the vicinity of the distance (time delay) of the received signal from the transducer. The nominal distance (time delay) of the sound traveling from the transducer to the microphone could be obtained automatically for the majority of seams by removing the compartment. If the microphone is close to the seam, the direct distance measured without the compartment is nearly the same as the distance through a leak in the seam.

The present invention utilizes the transmission of high frequency sound directed towards the leak areas and robot manipulated microphones to search for and detect sound leakage emanating from the other side of the barrier or enclosure which is under inspection. In such a scenario, an appreciable amount of interference is also received by the microphone which, in the absence of the present invention, may cause either false leak indications or no leak indication when a leak is actually present. The present invention overcomes this problem by specific design methods which reduce the effects of this interference. The resultant ratio of leak signal level to interference signal level is thereby maintained sufficiently high so as to insure high leak detection probability with acceptably low false alarm rates. The specific interfering signals, whose effect the present invention seeks to minimize, include the following:

1. External ultrasound interference received by the microphone and generated by various coincidental sources such as air hoses, arc discharges and other audible activities emanating broadband acoustic noise.
2. Self-induced interference received by the microphone as a result of permeation of the system transmitted ultrasonic energy directly through the "skin" of the enclosure, even in the absence of a leak opening. For purposes of this description, such interference will be referred to as skin leakage.
3. Self-induced interference received by the microphone as a result of the system transmitted ultrasonic energy reaching the microphone by passing through normal openings in the subject object or enclosure and reflecting off nearby objects and, thereby, into the microphone. For purposes of this description, such interference will be referred to as bounce-path interference.
4. Self-induced interference received by the microphone as a result of the system transmitted ultrasonic energy reaching the microphone via diffraction effects when the microphone is positioned to sense for a leak defect which is near a normal opening in the enclosure or object through which the transmitted energy will normally pass.

As another requirement of the system, it is necessary that automated means be implemented to periodically verify that the system transmitter(s) and microphone(s) are operative, and that the receiver processing circuits are operative. The present invention achieves this via a mode of operation wherein the transmitted signals are received and processed when the subject object or enclosure is not present. The character of the processed signals is analyzed by the system and sufficient data is thereby provided to verify operability of all components or localize a failure to a specific component.

As a further requirement of the system, it is necessary that a plurality of transmitters be provided to assure sufficient illumination of all potential leak areas on the object or enclosure, and that a plurality of robot-manipulated microphones be provided to enable sufficient microphone access to all leak areas within a defined process limited inspection time. The present invention provides this capability through the use of as many as four (4) robots and associated microphones, a multiplexed processing system capable of receiving and processing as many as four (4) microphone signals in real time, and signal processing methods which enable each of the four multiplexed processing channels to be sensitive only to transmitted energy from specific transmitters.

The invention will hereafter be described with reference to an exemplary embodiment, as illustrated in the drawing. However, it is to be understood that this embodiment is illustrated and described for the purpose of information only, and that nothing therein is to be considered limiting of any aspect of the invention.

DESCRIPTION OF THE PREFERRED EMBODIMENT

Although the present invention will be described with respect to its use in sensing leaks in auto bodies, it will be appreciated that it may also be utilized to detect leaks in other objects or enclosures.

Figure 1:
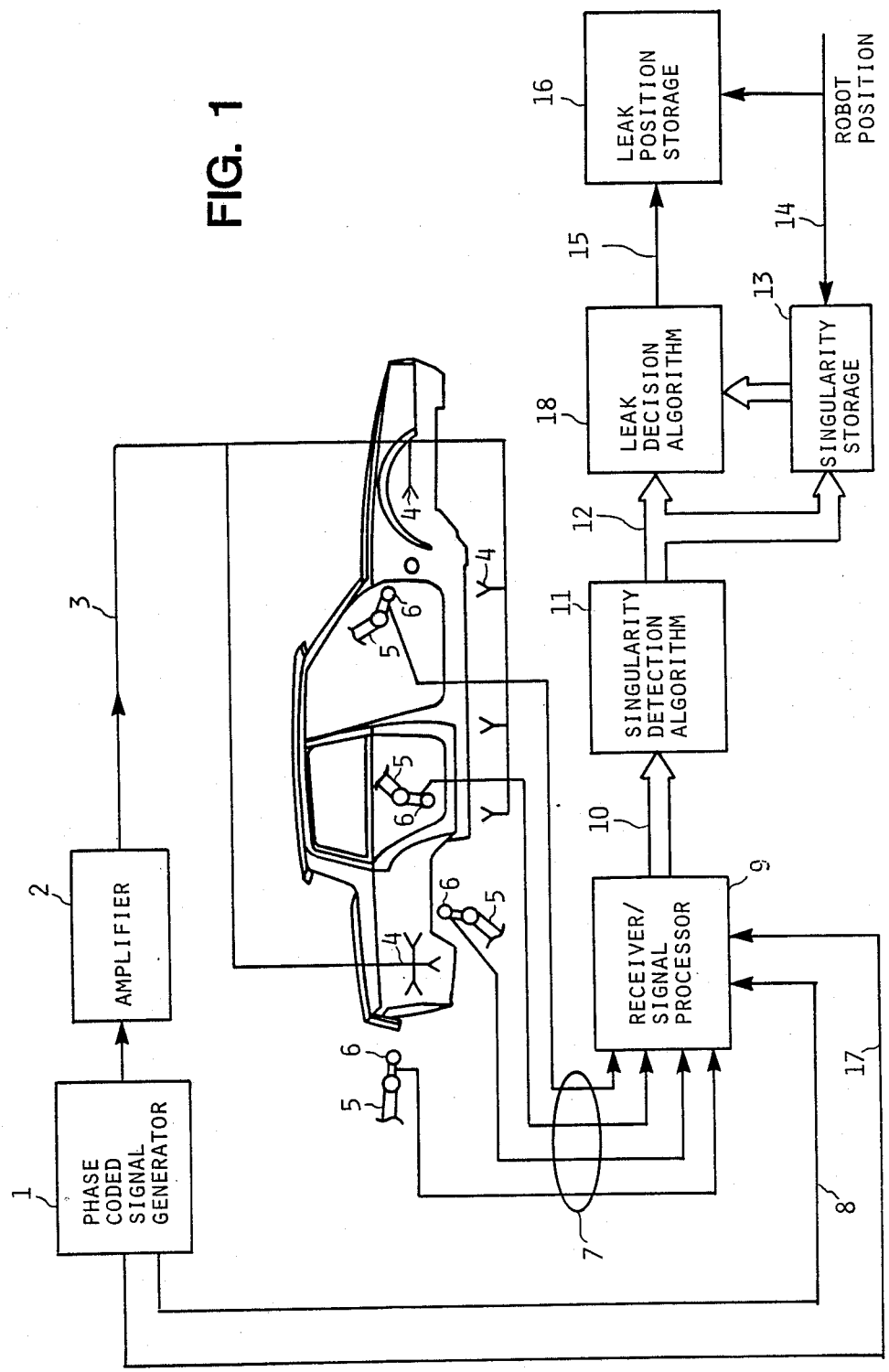
FIG. 1 shows a schematic view of the leak detection system in accordance with the present invention.

The system of the present invention operates as depicted in FIG. 1 and described herein with references to FIG. 1. A phase-coded signal generator (1) produces a high frequency signal with a carrier frequency, typically 75 KHZ, whose phase is sequentially reversed in accordance with a continuous pseudo random code (typically at a 10 KHZ rate). The carrier frequency is selected to minimize the interfering effects of skin leakage as previously defined, and to benefit from the greater atmospheric attenuation of inband factory noise, while the phase reversal coding is implemented to minimize the interfering effects of previously defined bounce path and diffraction types of interference. This coded signal enables discrimination against these latter forms of interference, based upon their time of arrival at the receiving microphones. The output of the phase-coded signal generator is amplified in power amplifier (2) which provides sufficient power (3) to excite transmitting transducers (4). These transducers convert the electrical signal (3) into ultrasonic energy for illumination of the potential leak areas. They each must have both sufficient transmitting beamwidth to provide a broad illumination pattern as required for proper coverage of all leak areas, as well as sufficient transmitting frequency bandwidth (typically 20 KHZ) to support the bandwidth of the coded transmitted signal.

The receiving microphones (6) are each manipulated by robot arms (5) along the areas of potential leaks. Four such robot/microphone subsystems can be accommodated by the system described herein. Each microphone (6) consists of a receiving transducer to convert the impinging sonic pressure waves to an electrical signal, and a low noise - high gain amplifier to provide sensitive reception and high level signals (7) which are more immune to corruption due to attenuation or noise pickup in the long cables which are required to reach from the robots to the centralized receiver/signal processor (9). In the processor (9), these received signals (7) are each heterodyned with the unmodulated carrier frequency (8) down to "baseband", such that only the received pseudo-random code and receiver noise remains. Each of these coded signals are sequentially time-multiplexed and converted to a digital format by a sampling 12 bit A/D converter which, therefore, outputs a serial digital bit stream which is fully representative of the received codes and noise. The receiver/signal processor (9) then performs a digital cross-correlation of these received codes with the transmitted pseudo random code. The resultant cross-correlation function in digital format (10) exhibits a maximum at correlation time delays which correspond to the acoustic transit delay time between the transmitting transducer and the receiving microphone. A time reference signal (17) is provided to the receiver/signal processor (9) by phase-coded signal generator (1).

In the above-described system implementation, the positions of the transmitters are fixed and thereby known, the positions of the robot-manipulated microphones can be continuously known via robot supplied position data, and the positions of the potential leak defects are also known. It is therefore possible to predict the total acoustic transit delay time for a true leak signal. The cross-correlation function (10) outputted by the receiver/signal processor (9) effectively separates the received signals in time, based upon their acoustic transit time. Since for true leak signals this transit time is predictable as argued above, such signals can be isolated by inspecting the cross-correlation function for a maximum at the proper predictable correlation time (typically within ±3.5 inches). Maximums observed at other correlation times can be effectively ignored as resulting from other acoustic interference paths such as diffraction and bounce paths, or as being received from another transmiter in the system. Thus, the present invention has the inherent capacity of discriminating against these sources of system self interference through the effective use of time-delay discrimination.

The particular implementation employed to achieve this capability in the present invention requires further explanation at this point. The use of coded continuous wave signals is required by overall energy requirements. The requirement for high leak detection probability with low false alarm rates dictates that the leak signal to system noise ratio be high at the leak/no leak decision point. For a system designed to optimize this ratio, the signal to noise ratio S/N is:

$$S/N = KEr/n$$

where:
Er = total leak energy received by the microphone
n = effective noise energy at the microphone due to all system electrical noise and received acoustic noise
K = a proportionality factor While n can be minimized by careful receiver design to reduce electrical noise, received acoustic noise may be impractical to combat in practical industrial environments. Thus, it is critical that received energy (Er) be maximized to optimize system performance on the smallest leaks.

Since available transmitters are peak-power limited, available energy is maximized in the present invention by phase-encoding a CW signal over a long period of time. Range discrimination is then recovered by correlation of the received signal with a reference signal that is a copy of the transmitted signal.

Figure 2:
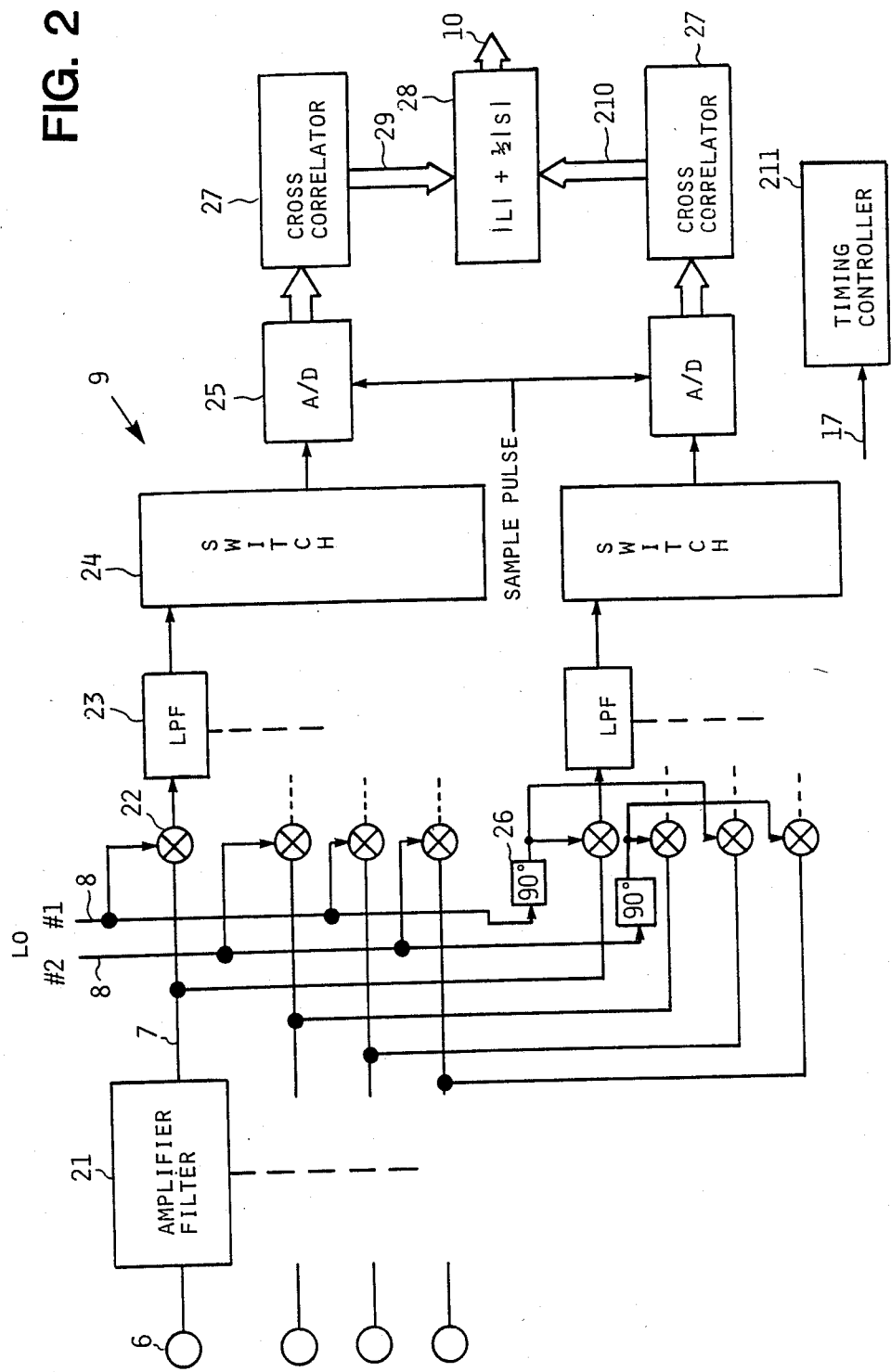
FIG. 2 shows a block diagram of the receiver/signal processor.

FIG. 2 provides greater detail of the processing within Receiver/Signal Processor 9 and the signal pickup. Each microphone 6 is followed by an amplifier/filter 21 having typically 60db gain and 20 KHZ bandwidth centered at the carrier frequency. The signals 7 are hetrodyned to baseband by mixers 22 that are driven by local oscillator signals 8 that are unmodulated samples of the transmitted carrier waveform. Provision for two separate local oscillator (LO) frequencies is shown. Two identical processing channels are provided, an in-phase and a quadrature channel. The in-phase channel receives the output of a mixer 22 excited directly by local oscillator power 8. The quadrature channel receives the output of a similar mixer. However, local oscillator power 8 is first shifted 90° by phase shifter 26 as is well known in the art. The mixer 22 output is then low-pass filtered by Filter 23 and time multiplexed at a rate eight times that of the code bit rate by switch 24. A/D converter 25 converts the sample amplitude into a digital word which is fed to cross-correlator 27. The output 29 of cross-correlator 27 is combined with a similar signal 210, developed by the quadrature channel, in a Quadrature Combiner 28. Combiner 28 approximates the vector sum of the two signals using the approximation of adding the magnitude of the larger of the two signals to one-half of the magnitude of the smaller signal, producing output 10. The quadrature signal 210 is generated in the same manner as described above for the in-phase signal between mixer 22 and cross correlator 27. The phase shift of 90° introduced into the Local Oscillator signal 8 provides the quadrature phase shift needed to optimally detect the received signal with unknown phase.

A timing controller 211 provides all needed timing signals necessary to operate switches 24, converters 25, correlators 27 and combiner 28. The timing signals are synchronized to signal generator 1 by time reference signal 17.

Figure 3:
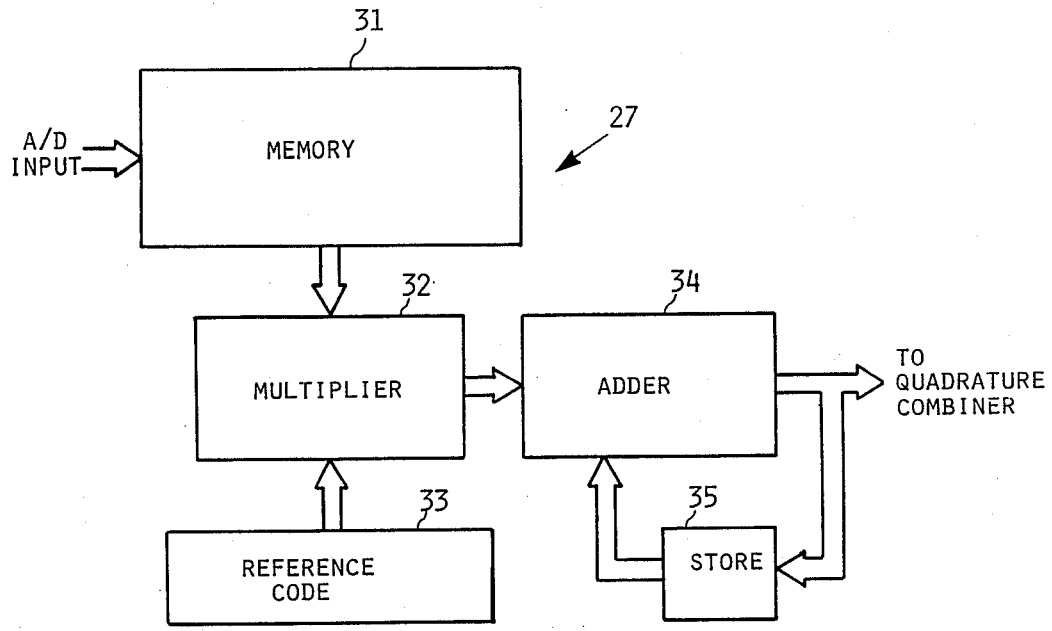
FIG. 3 shows a block diagram of the cross-correlator.

FIG. 3 provides greater detail on cross correlator 27. The digital words representing signal amplitudes from A/D converter 25 is stored in memory 31. The received signal is continuously received as the microphone scans a seam. Memory 31 is organized preferably as a circular buffer, overwriting data too old to be of interest. After storing a complete-received code length in memory 31, samples are read from memory and multiplied by +or −1 according to the reference code 33 by multiplier 32. This output is accumulated over the code length (255 samples has been successfully used) by adder 34 and storage 35 arranged in a loop. Storage 35 stores 8 words so that the eight multiplexed values are accumulated for each code bit. At the end of the code length, the accumulated values are sent to the Quadrature Combiner 28 and the storage 35 is zeroed to repeat the process for the next reference code. Correlations are thus performed for received signal transit time delays of from zero to 4 msec, corresponding to acoustic path lengths of from zero to approximately 4 feet.

Output 10 from Receiver/Signal Processor 9 is then thresholded by Singularity Detection Algorithm 11. Algorithm 11 uses a noise average to set a lower limit on declaring a signal present. At short distances (shorter than the transmitter to microphone direct-path delay) it is known that no true signal exists. Therefore whatever is received can be considered as noise. A singularity is declared as any sample interval (cell) that exceeds the level of samples just prior to and following the sample. In the event that two or more samples have identical levels, then those cells are declared a singularity if their level exceeds the level of samples just prior to and following the group. Next, the smaller level of the two samples surrounding the central cell(s) is subtracted from the level of the central cell(s). If the difference exceeds a preset multiple of the average noise level (or a fixed threshold if the noise average falls below it), then the singularity is passed as output 12 to Singularity Storage 13 to form a reference when in a training mode, or to Leak Decision Angorithm 18 when in an inspection mode.

Singularity Storage 13 retains a record of the amplitude and transit time of all singularities detected in the learning mode (i.e. an inspection of a "leak free" object). Robot position from input 14 is also stored for all detected singularities.

In the inspection mode, Leak Decision Algorithm 18 uses the stored reference in Singularity Storage 13 to determine if a reported singularity 12 is part of the normal signal pattern or a detected leak. Algorithm 18 allows tolerances on the received signal to account for unavoidable variations in the manufacturing and inspection processes. New singularities or singularities significantly larger than the reference are declared leaks. A ±2 sample shift in time from the reference is allowed. If the first singularity in range (distance from transmitter) is within ±2 cells of the first reference singularity and less than twice the size of the reference, it is ignored and the algorithm repeated on the next singularity in range up to the maximum range. Any singularity not ignored is classified as a potential leak. Since the robot scan is made slow compared to the processing time, multiple samples are obtained on any leak. If a location is declared to have a potential leak in 3 out of 5 successive processing times (separate in time sufficient for statistical independence), a leak is declared and passed on as signal 15 to Leak Position Storage 16. Storage 16 also records the robot position 14 of the declared leak.

The ability of the modulated waveform to discriminate signals having different acoustic transit times from transmitter to receiver enables automatic verification of component performance. Since the distance to be traveled by the primary path is known, the failure of the measured data to indicate a signal at that distance provides a reliable indication of a malfunctioning system which can alert an operator that a problem exists.

Figure 4:
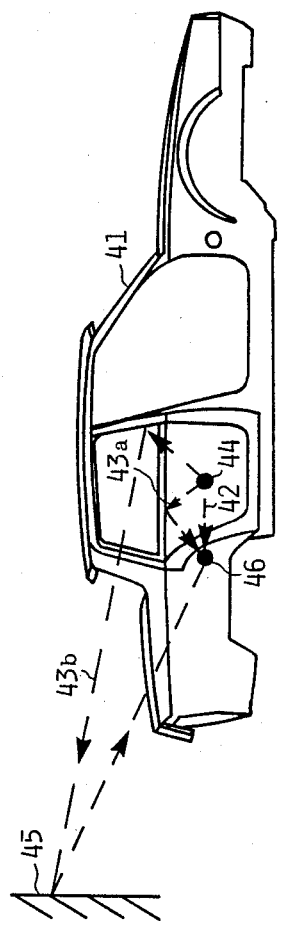
FIG. 4 shows three paths for sound to travel in a representative application.

A second preferred embodiment uses linear frequency modulation to reduce the multipath interference of transmitted energy. FIG. 4 illustrates a typical system installation.

Vehicle 42 has a source of sonic energy 44 placed within it, with expectation that the energy will travel directly via path 41 and through the leak opening to sonic detector 46. However, the energy cannot be confined to primary path 42 alone and finds other paths such as paths 43a and 43b. The energy following path 43a bounces off internal structures and then through the leak opening to sonic detector 46. Thus the leak signal consists of the vectorial summation of signals from primary path 42 and all internal bounce paths such as 43a. At any constant transmitted frequency, this vector summation can result in a null when individual amplitudes are comparable and phase differences approach 180°. In such cases, the effective leak signal is suppressed and missed detections can result. In addition to this effect, energy can enter sonic detector 46 via external bounce path 43b which does not pass through the leak opening but rather through the normal openings in the vehicle. Such interference is present independent of leak openings and results in a relatively high level background interference which masks the small sonic energy passing through the leak opening. Thus, leak detection improvement must both eliminate the leak signal nulling effects due to anomalous internal paths 43a, as well as the leak signal masking effects due to anomalous external paths 43b.

In the prior art, only the nulling effects of paths 43a were dealth with. This was accomplished by sinusoidal modulation of the transmitted sonic frequency. Since nulls can only occur at certain discrete frequencies as previously indicated, any form of frequency modulation will prevent continuous nulling. The signal vector summation will alternately pass through nulls and peaks at the modulation frequency. The peaks can thus be effectively detected as leaks, providing that they sufficiently exceed the background interference due to external bounce paths 43b. This solution did not address this latter effect, and the leak signal could not be distinguished from this interfering background level.

The present invention provides the facility to make this distinction by linearly changing the transmitted frequency. For all paths greater than a given distance, the path time delay causes the received signal to be at a frequency far enough from the transmitting frequency to allow blocking the unwanted signal by a low pass filter.

Figure 5A:
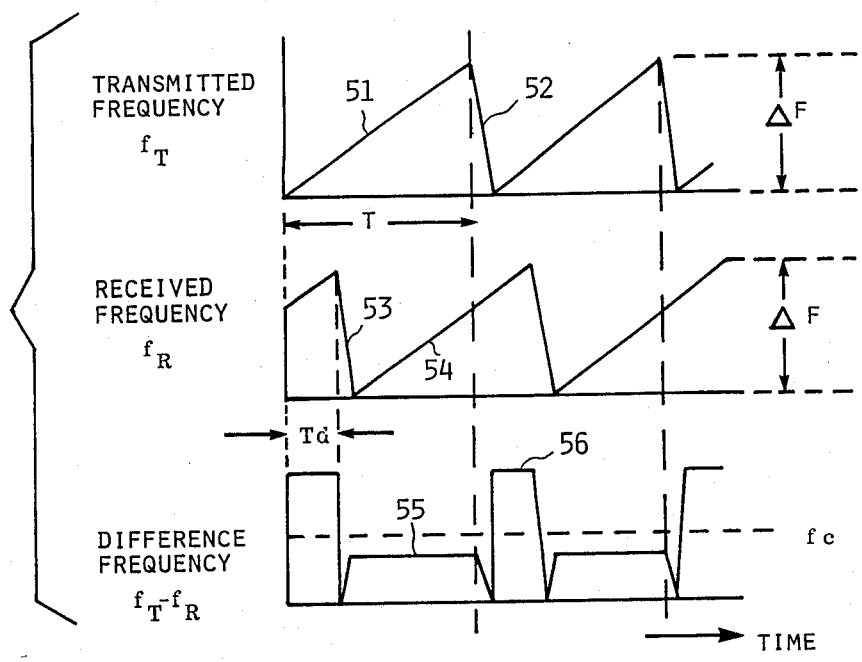
FIG. 5a illustrates the linear frequency modulation of the invention source with a time-delayed return signal and the difference in frequency as a result of hetrodyning.

FIG. 5a illustrates the present invention preferred modulation. The transmitted frequency $f_t$ is linearly changed 51 during a time T, then rapidly brought back 52 to the starting frequency, and the cycle repeated continuously. The amount of frequency deviation $\Delta F$ can be varied to increase or decrease the frequency difference between the transmitted frequency and a time-delayed received frequency $f_r$. For a time delay $T_d$ between transmitting the signal and receiving the signal with a transmitted rate of frequency change $= \Delta F/T$, the frequency difference is equal to $(\Delta F/T)T_d$.

Figure 5B:
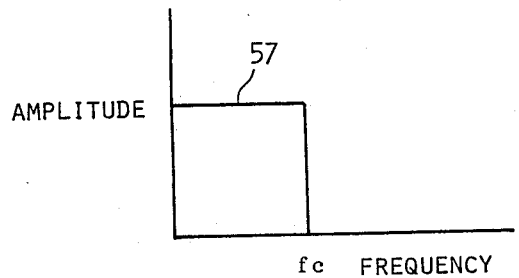
FIG. 5b illustrates a low pass filter characteristic used for removing undesired signals.

By making sweep time T long compared to the time delay $T_d$ of expected leak signals, the difference frequency portion 55 will be long compared to portion 56. Portion 55 will have a frequency $f_t - f_r$ that is a function of the design parameters and the distance the signal travels. Signals traveling further than a known maximum design distance must represent interfering multipath signals and should be eliminated. By passing the signals through a low pass filter whose idealized characteristic is given in FIG. 5b, signals above frequency $f_c$ will be attenuated sufficiently to remove them from competing with the signals below that frequency (response level 57). The frequency deviation $\Delta F$ is selected to make the maximum design distance return a signal differing from the transmitted frequency by $f_c$. The frequency difference 56 is equal to $\Delta F(1 - T_d/T)$ which is well beyond fc (for $T_d$ small compared to T) and is therefore filtered out.

Figure 6:
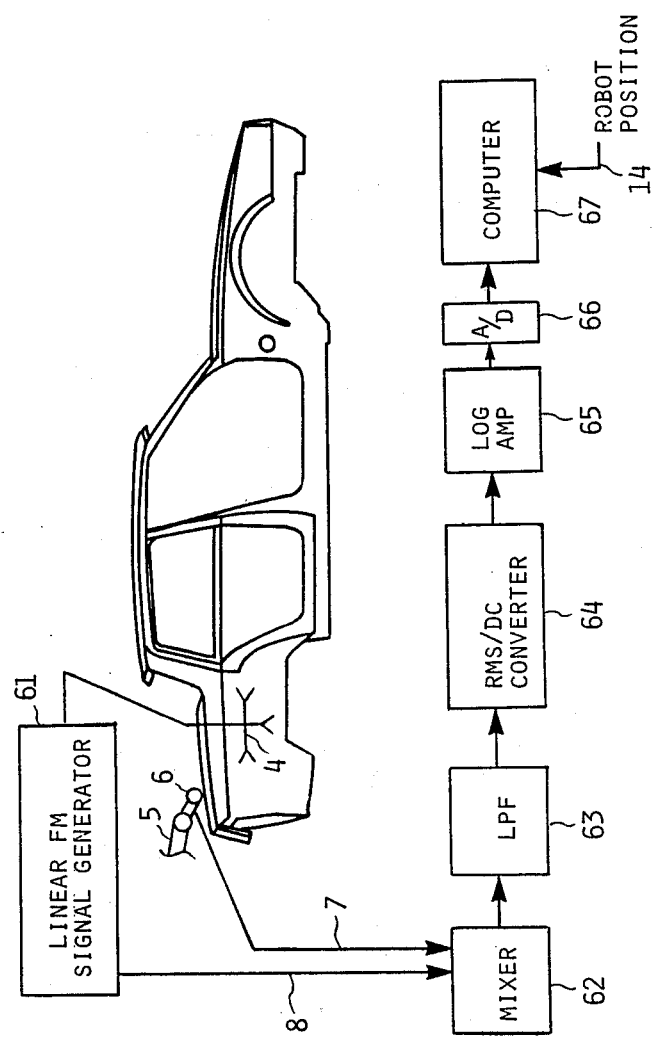
FIG. 6 illustrates a leak detection system employing linear FM range discrimination.

FIG. 6 illustrates the use of the linear FM method in providing a computer 67 with amplitude data proportional to signal power emitted from transmitting transducers 4 and traveling, via leaks in seams of a vehicle being inspected, to a microphone 6 on robot arm 5. Linear FM Signal Generator 61 provides the linearly swept signal transmitted by transducers 4 and a sample of the transmitted frequency 8 to serve as a local oscillator signal in mixer 62. Output signal 7 from microphone 6 is multiplied in mixer 62 by local oscillator 8 to provide a difference frequency signal. The difference frequency signal is filtered by low-pass filter 63 to remove all frequencies above a frequency corresponding to the maximum expected time delay of the received signal 7. The filtered signal is converted to a D.C. signal in converter 64, amplified logarithmically by amplifier 65, and converted to a digital signal by A/D converter 66. Digital computer 67 then stores the signal with the robot position data 14 to generate reports regarding the detected leaks.

In both methods described, the phase or frequency modulation has been implemented in a manner to provide signal discrimination as a function of time of travel of the sound from transmitter to receiver. This enables an improved sensitivity of detecting leak signals, and increases the reliability of the signal patterns received as the microphone is scanned along seams. By recording these patterns on a sample produce with no leaks, an automatic calibration mode is provided. During inspection of similar products, leaks can be declared to exist wherever significant deviation exists from the recorded reference patterns.

Also, since the received signal is a direct function of the distance from the transmitter to the receiver, the product can be removed and a closed loop system component test can be run and faults readily located.

Finally, the system allows for small deviations in the robot paths since no critical adjustments have to be made for satisfactory performance. Needed tolerances on transmitted signal path changes can be readily designed into the system with very small negative effect on performance.

The invention has been described and illustrated with reference to an exemplary embodiment. It is not to be considered limited thereto, inasmuch as all modifications and variations which might offer themselves are intended to be encompassed within the scope of the appended claims.

What is claimed is:

1. A method for detecting regions of imperfect sealing along seams formed by overlapping sheet materials that would allow gas or liquid penetration, comprising the steps of: generating a modulation code; generating ultrasonic energy; modulating said energy by said modulation code; illuminating one side of a reference seam to be inspected with the modulated ultrasonic energy; transporting a microphone on the opposite side of said reference seam by a robotic positioner; processing the output signal of said microphone to enhance the signal to noise ratio; detecting singularities in said signal; recording said singularities as reference singularities; repeating the steps of illuminating, transporting, processing and detecting on a seam similar to said reference seam; comparing said detected singularities with said recorded reference singularities; and declaring as imperfect any region containing a new singularity or significantly larger singularity.

2. A method as defined in claim 1, wherein said modulation code is a pseudo-random code.

3. A method as defined in claim 1, wherein said step of modulating said energy comprises phase modulation.

4. A method as defined in claim 1, wherein the microphone output signal processing step comprises: hetrodyning said signal to baseband and producing a baseband signal and cross-correlating said baseband signal with said modulation code.

5. A method as defined in claim 1, wherein the microphone output signal processing step comprises: hetrodyning said signal to baseband, forming an in-phase and quadrature signal component; cross-correlating said signals with said modulation code; and vectorily combining the cross-correlation output signals.

6. A method as defined in claim 1, wherein said step of detecting singularities comprises: determining an average noise level in said signal for a given distance from a source of modulated sonic energy; determining a distance interval at which said signal has a level exceeding the level of said signal at adjacent closer and further distance; subtracting the smaller signal level of said adjacent closer and further distances from the signal level of said distance interval and forming a difference level from said subtracting step; and declaring a singularity if said difference level exceeds a predetermined multiple of said average noise level and a predetermined threshold level.

7. A method as defined in claim 1, wherein said singularity detection occurs at discrete distance intervals and said comparing step comprises: testing in a first test if a reference singulatity with an amplitude of half or more of the amplitude of a detected singularity is at the same distance; repeating in a second test said first test at one said discrete distance interval shorter distance if said first test fails; repeating in a third test said first test at one said discrete distance interval greater distance than said detected singularity if said first and second tests fail; declaring a leak candidate at said detected distance if all said three tests fail; repeating for all detected singularities; and declaring a new singularity if a specified number of leak candidates are declared out of a predetermined number of statistically independent measurements at a common distance.

8. An arrangement for detecting regions of imperfect sealing along seams formed by overlapping sheet materials that would allow gas or liquid penetration comprising: means for generating a pseudo random modulation waveform; means for generating a carrier signal; means for modulating said carrier signal by said modulation waveform; transducer means for generating ultrasonic energy by said modulated carrier signal; means for directing said ultrasonic energy toward one side of a seam to be investigated; robotic positioner means; sonic energy detecting means transported on the opposite side of said seam by said robitic positioner means;

signal processing means for enhancing the signal to noise ratio of a signal from said detecting means; computation means for detecting and recording a reference signal pattern; computation means for comparing a detected signal with said reference pattern to declare singularities; and storage means for recording said robotic positioner means position and said singularities.

9. An arrangement as defined in claim 8, wherein said modulating said carrier signal comprises phase-encoding.

10. An arrangement as defined in claim 8, wherein said signal processing means comprises: an amplifier; a bandpass filter; mixing means for hetrodyning signals derived from said detecting means to baseband; and means for cross correlating said baseband signal with said modulation waveform.

11. An arrangement as defined in claim 10, wherein said mixing means provides an in-phase and quadrature component of said baseband signals; means for cross-correlating said in-phase and said quadrature components with said modulation waveform; and means for vectorily combining outputs of said cross-correlating means.

12. A method for detecting regions of imperfect sealing along seams formed at the juncture of two materials that would allow gas or liquid penetration comprising the steps of: generating a periodic modulation waveform with specified period; providing a source of acoustic energy; frequency modulating said acoustic energy by said modulation waveform; illuminating one side of a reference seam with said modulated acoustic energy; transporting an acoustic sensor along the opposite side of said seam; multiplying the signal output of said acoustic sensor by a signal proportional to said modulated acoustic energy; filtering the signal generated by multiplying to attenuate frequencies greater than a predetermined value; recording said filtered signal to provide a reference record; repeating the illuminating, transporting, multiplying filtering and recording steps on a seam to be inspected to provide an inspection record; and declaring leaks at locations where said inspection record signal is greater than said reference record signal by a designated amount.

13. A method as defined in claim 12, wherein said frequency modulating step comprises a sawtooth.

14. A method as defined in claim 12, wherein said transporting step is carried out by a robotic positioner.

15. A method as defined in claim 13, wherein a predetermined amount of frequency deviation is used for causing the signal generated by multiplying to be greater than a predetermined frequency for a given distance traveled by said acoustic energy from said acoustic source to said acoustic sensor.

* * * * *